(12) United States Patent
Mathur

(10) Patent No.: US 6,251,425 B1
(45) Date of Patent: Jun. 26, 2001

(54) GLUCOSIDE PAUCILAMELLAR VESICLES

(75) Inventor: Rajiv Mathur, Sewell, NJ (US)

(73) Assignee: Igen, Inc., Wilmington, DE (US)

( * ) Notice: Subject to any disclaimer, the term of this patent is extended or adjusted under 35 U.S.C. 154(b) by 0 days.

(21) Appl. No.: 09/165,436

(22) Filed: Oct. 2, 1998

(51) Int. Cl.$^7$ .............................. A61K 9/127; A61K 7/00
(52) U.S. Cl. .................. 424/450; 424/401; 428/402.2; 514/725
(58) Field of Search .................. 424/450, 401, 424/1.21, 9.321, 9.51, 417, 94.3; 428/402.2; 436/829; 935/54; 514/725, 844–848, 937

(56) References Cited

U.S. PATENT DOCUMENTS

| | | | |
|---|---|---|---|
| 4,614,796 | * 9/1986 | Kawamate . | |
| 4,873,035 | 10/1989 | Wong | 264/4.6 |
| 5,160,669 | 11/1992 | Wallach et al. | 264/4.3 |
| 5,229,104 | 7/1993 | Sottery et al. | 424/59 |
| 5,234,767 | 8/1993 | Wallach | 428/402.2 |
| 5,260,065 | 11/1993 | Mathur et al. | 424/450 |
| 5,405,615 | 4/1995 | Mathur | 424/450 |
| 5,411,742 | 5/1995 | Sebag et al. | 424/450 |
| 5,439,967 | 8/1995 | Mathur | 424/450 |

FOREIGN PATENT DOCUMENTS

| | | |
|---|---|---|
| 19634374 | 3/1998 | (DE) . |
| 0 301 333 A2 | 7/1988 | (EP) . |
| 0 317 803 B1 | 5/1993 | (EP) . |
| 0 267 050 B1 | 9/1994 | (EP) . |
| 2135878 | 9/1984 | (GB) . |
| 10087684 | * 4/1998 | (JP) . |
| 93/03709 | 3/1993 | (WO) . |
| 93/08202 | 4/1993 | (WO) . |
| WO 9513052 | 5/1995 | (WO) . |

OTHER PUBLICATIONS

Kiwada, H. et al. "Application of Synthetic Alkyl Glycoside Vesicles as Drug Carriers. I. Preparation and Physical Properties" *Chem. Pharm. Bull.* 33(2):753–759 (Feb. 1985).

* cited by examiner

*Primary Examiner*—Gollamudi S. Kishore
(74) *Attorney, Agent, or Firm*—Lahive & Cockfield, LLP

(57) ABSTRACT

Paucilamellar lipid vesicles containing lipid bilayers at least two lipid bilayers formed of surfactant materials, each of the bilayers comprising a glucoside primary amphiphile and a steroid. The vesicles may have either an aqueous or oil-filled central cavity and are particularly useful for delivering dermatological, cosmetic and pharmaceutical formulations. A method of manufacture for these vesicles is also disclosed.

10 Claims, No Drawings

GLUCOSIDE PAUCILAMELLAR VESICLES

BACKGROUND OF THE INVENTION

The present invention relates to formulations for lipid vesicles and methods of their manufacture. More particularly, the present invention discloses paucilamellar lipid vesicles designed of materials which have exceptional properties for cosmetic, edible, dermatological, and pharmaceutical use.

Lipid vesicles are substantially spherical structures made of amphiphiles, e.g., surfactants or phospholipids. The lipids of these spherical vesicles are generally organized in the form of lipid bilayers, e.g., multiple onion-like shells of lipid bilayers which encompass an aqueous volume between the bilayers. Paucilamellar lipid vesicles have 2–10 peripheral bilayers which surround a large, unstructured central cavity.

Until recently, liposome technology has been concerned mostly with vesicles composed of phospholipids. This is primarily because phospholipids are the principal structural components of natural membranes and, accordingly, lipid vesicles have been used as a model system for studying natural membranes. However, there are a number of problems associated with using phospholipids as synthetic membranes. Biological membranes are stabilized by membrane proteins and maintained by extensive enzymatic "support" systems that rapidly turn over, exchange or modify membrane lipids. Neither membrane proteins nor the requisite enzymatic support systems can be practically incorporated into the wall structure of liposomes, making the structures inherently less stable than natural membranes. In addition, the biological environment contains several potent phospholipases that rapidly break down free phospholipids. These phospholipids will attack liposomes and degrade the membrane. For these reasons, phospholipid liposomes are rapidly degraded in vivo.

Moreover, phospholipid liposome technology has other problems. Phospholipids are labile and expensive to purify or synthesize. In addition, classic phospholipid liposomes are in the form of multilamellar as opposed to paucilamellar vesicles and have poor carrying capacities, especially for lipophilic materials, and have poor shelf lives unless lyophilized in the dark with antioxidants. Finally, phospholipids degrade too rapidly in vivo for most pharmaceutical or vaccine applications. For these reasons, there is increasing interest in the art for paucilamellar lipid vesicles made of other amphiphilic compounds.

SUMMARY OF THE INVENTION

The present invention features lipid vesicles and a methods of their manufacture employing certain glucosides as primary wall formers. These vesicles feature materials with special usefulness for cosmetic and dermatological processes and products.

The vesicles in the invention generally have two to ten bilayers arranged in the form of substantially spherical shells separated by aqueous layers surrounding a large amorphous central cavity free of lipid bilayers. The lipid bilayers have as their primary wall components a mixture of a glucoside primary amphiphile, or wall former, and a steroid such as cholesterol. The glucoside primary amphiphile is not believed to form vesicles in the absence of the steroid. The vesicles may optionally comprise a minor amount of a secondary amphiphile, e.g., which improves the shelf life stability of the vesicles, such as $C_{12}$–$C_{18}$ fatty alcohols, polyoxyethylene acyl alcohols, polyglycerols, sorbitan fatty acid esters, ethoxylated sorbitan fatty acid esters, $C_{12}$–$C_{18}$ glycol monoesters, $C_{12}$–$C_{18}$ glyceryl mono- and diesters, propylene glycol stearate, sucrose distearate, glyceryl dilaurate, and mixtures thereof.

In an embodiment the glucoside is a fatty glucoside, e.g., cocoyl glucoside, arachidyl behenyl glucoside, cetearyl glucoside, myristyl glucoside or mixtures thereof. In certain embodiments, the lipid bilayer may comprise a certain amount of the alcohol corresponding to the fatty acid portion of the glucoside, e.g., myristyl alcohol.

In an embodiment the steroid may be a sterol, such as cholesterol, cholesterol derivatives, hydrocortisone, phytosterol, and mixtures thereof. In other embodiments, other additives such as charge producing agents, and other lipid soluble materials may be incorporated into the vesicles.

DETAILED DESCRIPTION OF THE INVENTION

The present invention uses a blend of amphiphiles to form paucilamellar lipid vesicles. In particular, a glucoside such as a fatty glucoside is combined with at least one steroid such as cholesterol to form a lipid phase which can be hydrated to form vesicles. Minor amounts of other additives such as $C_{12}$–$C_{18}$ fatty alcohols may also be blended with the lipid phase.

The lipid vesicles disclosed herein are paucilamellar lipid vesicles generally characterized as having two to ten lipid bilayers or shells with small aqueous volumes separating each substantially spherical lipid shell. The innermost lipid bilayer surrounds a large, substantially amorphous central cavity which may be filled with either an aqueous solution or a water-immiscible oily solution.

The lipid bilayers have as their primary wall components a mixture of a glucoside primary amphiphile (or wall former), and a steroid such as cholesterol. The glucoside primary amphiphile is not believed to form vesicles in the absence of the steroid. In a preferred embodiment, the glucoside primary amphiphile may be a fatty glucoside, e.g., where the fatty portion of the glucoside is derived from a $C_{10}$ to $C_{50}$ fatty acid. Exemplary glucoside primary amphiphiles include cocoyl glucoside, arachidyl behenyl glucoside, cetearyl glucoside and myristyl glucoside, and mixtures thereof. The lipid bilayers generally comprise up to 75% of glucoside primary amphiphile.

Preferred steroids include sterols including cholesterol, cholesterol derivatives, ethoxylated cholesterol, hydrocortisone, phytosterol, and mixtures thereof. The amount of sterol may depend up to some extent on whether it competes with any lipophilic material to be encapsulated. In an embodiment, the lipid bilayers generally comprise about 0–25% of a steroid such as a sterol.

The vesicles may optionally comprise a minor amount of a secondary amphiphile, e.g., which improves the shelf life stability of the vesicles likely by altering the phase transition of the vesicles. Also, in certain applications incorporation of the secondary amphiphile may modulate penetration of the encapsulated active molecule through skin. Exemplary secondary amphiphiles include $C_{12}$–$C_{18}$ fatty alcohols, polyoxyethylene acyl alcohols, polyglycerols, sorbitan fatty acid esters, ethoxylated sorbitan fatty acid esters, $C_{12}$–$C_{18}$ glycol monoesters, $C_{12}$–$C_{18}$ glyceryl mono- and diesters, propylene glycol stearate, sucrose distearate, glyceryl dilaurate, and mixtures thereof.

The lipid bilayers may also comprise about 0–5% of a charge-producing agent such as dicetyl phosphate, quaternary ammonium salts, cetyl sulfate, sarcosinamides, phosphatidic acid, phosphatidyl serine, and fatty acids such as oleic acid or palmitic acid.

Examples of water-immiscible oily materials which can be encapsulated in the central cavity are mineral oils, soybean oil, paraffin waxes, petrolatum, triglyceride oils and fats, perfumes and fragrances, flavor oils, perfluorocarbon liquids, anthralin, retinoic acid, water insoluble vitamins, and water immiscible solvents. Avocado oil unsaponifiables can also be encapsulated in the central cavity and are particularly useful, as they may additionally be used as a source of phytosterol for stabilizing the vesicle bilayer(s).

Oil filled vesicles, e.g., vesicles having their amorphous central cavities filled with a water-immiscible oily solution, may be formed using either the "hot loading" technique disclosed in U.S. Pat. No. 4,911,928 or the "cold loading" technique described in U.S. Pat. No. 5,160,669, the disclosures of which are incorporated herein by reference. In either case, a lipid phase is formed by blending a glucoside primary amphiphile and the compatible amphiphile(s), along with any sterols or lipophilic materials to be incorporated into the lipid bilayers, to form a homogenous lipid phase. In the "hot loading" technique, any water-immiscible oily material to be encapsulated in the vesicles is blended in the already formed lipid phase, forming a lipophilic phase. If any oil-soluble or oil-suspendable materials are to be encapsulated within the vesicles, they are first dispersed in the oil. The term "dispersed" as used herein includes dissolution or forming a suspension or colloid to yield a flowable phase.

Once a lipophilic phase is made, it is blended with an aqueous phase (e.g., water, saline, or any other aqueous solution which will be used to hydrate the lipids) under shear mixing conditions to form the vesicles. "Shear mixing conditions", as used herein, means a shear equivalent to a relative flow of 5–50 m/s through a 1 mm orifice. The paucilamellar lipid vesicles of the disclosure can be made by a variety of devices which provides sufficiently high shear for shear mixing. A device which is particularly useful for making the lipid vesicles of the present invention is described in U.S. Pat. No. 4,985,452, assigned to Micro Vesicular Systems, Inc.

In the "cold loading" technique, the lipid phase and the aqueous phase are blended under shear mixing conditions to form vesicles. Once the substantially aqueous filled lipid vesicles are formed, they are combined with the "cargo" material to be encapsulated, e.g., the water immisicible material. Droplets of the water immiscible material enter the vesicles, presumably by a process resembling endocytosis. The cold loading method has been described in more detail in the aforementioned U.S. Pat. No. 5,160,669. These vesicles are then blended under low shear conditions, as described in U.S. Pat. No. 5,160,669.

The invention is further illustrated by the following Examples, which should not be construed as further limiting the subject invention. The contents of all references, issued patents, and published patent applications cited throughout this application including the background are hereby incorporated by reference.

EXAMPLE 1

In this Example, paucilamellar lipid vesicles were made in accordance with this disclosure as follows.

TABLE 1

|  | Sample | | |
|---|---|---|---|
|  | A | B | C |
| Glucoside primary amphiphile (g) | | | |
| Myristyl glucoside[1] | 4.0 | | |
| Arachidyl behenyl glucoside[2] | | 4.0 | |
| Cocoyl glucoside[3] | | | 4.0 |
| Steroid (g) | | | |
| Cholesterol | 0.5 | 0.5 | 0.5 |
| Secondary amphiphile (g) | | | |
| Glyceryl dilaurate | 1.25 | 1.25 | 1.25 |
| Water | 50.0 | 50.0 | 50.0 |
| Encapsulated component(s) (g) | | | |
| Propylene glycol dicaprate/caprate[4] | 1.0 | 1.0 | 1.0 |
| Processing temperature, °C. (lipid) | 65 | 78 | 72 |
| Processing temperature, °C. (aqueous) | 60 | 70 | 68 |

[1]MONTANOV 14 (SEEPIC, Inc.), which includes a minor amount of myristyl alcohol
[2]MONTANOV 202, which includes a minor amount of arachidyl alcohol
[3]MONTANOV 82, which includes a minor amount of cetearyl alcohol
[4]CAPTEX 200.

For each sample, the vesicles were made by blending the amphiphiles and the cholesterol and then hydrating the formed lipid phase with water. Hydration to form lipid vesicles was achieved by shear mixing the lipid and aqueous phases using two 60 cc syringes, connected by a stopcock. The lipid and aqueous phases were blended from one syringe to the other, forming aqueous filled vesicles in two minutes or less. However, in this and the following Examples, any method of achieving the proper shear may be used. Preferably, a flow device such as the NovaMix™ vesicle former is used. The basic details of the NovaMix™ system are described in U.S. Pat. No. 4,895,452, the disclosure of which is incorporated herein by reference.

Microscopic examination of the resulting vesicles showed that sample A produced very good small, spherical homogeneous paucilamellar vesicles with some aggregation. Sample B produced good medium and small spherical paucilamellar vesicles with some aggregation. Sample C formed good small, spherical paucilamellar vesicles.

This Example shows that paucilamellar lipid vesicles in accordance with the disclosure may be formed by also including at least one other secondary amphiphile.

EXAMPLE 2

In this Example, lipid vesicles similar to those in Example 1 were made to demonstrate encapsulation of certain oils, e.g., propylene glycol dicaprate/caprate and mineral oil.

TABLE 2

|  | Sample | | | | | |
|---|---|---|---|---|---|---|
|  | A | B | C | D | E | F |
| Glucoside primary amphiphile (g) | | | | | | |
| Myristyl glucoside[5] | 4.0 | 4.0 | | | | |
| Arachidyl behenyl glucoside[6] | | | 4.0 | 4.0 | | |
| Cocoyl glucoside[7] | | | | | 4.0 | 4.0 |
| Steroid (g) | | | | | | |

TABLE 2-continued

| | Sample | | | | | |
|---|---|---|---|---|---|---|
| | A | B | C | D | E | F |
| Cholesterol | 1.0 | 1.0 | 1.0 | 1.0 | 1.0 | 1.0 |
| Encapsulated component(s) (g) | | | | | | |
| Propylene glycol dicaprate/caprate[8] | 20.0 | | 20.0 | | 20.0 | |
| Mineral oil | | 20.0 | | 20.0 | | 20.0 |
| Water | 50.0 | 50.0 | 50.0 | 50.0 | 50.0 | 50.0 |
| Processing temperature, °C. (lipid) | 75 | 75 | 75 | 75 | 75 | 75 |
| Processing temperature, °C. (aqueous) | 70 | 70 | 70 | 70 | 70 | 70 |

[5]MONTANOV 14
[6]MONTANOV 202
[7]MONTANOV 82
[8]CAPTEX 200

Sample A produced very good small, spherical homogeneous paucilamellar vesicles. Sample B produced larger spherical paucilamellar vesicles and smaller heterogeneous paucilamellar vesicles. Sample C produced larger, odd shaped but acceptable paucilamellar vesicles. Sample D produced more spherical paucilamellar vesicles in comparison to Sample C but of poor quality. Sample E produced very good small, spherical homogeneous paucilamellar vesicles. Sample F produced poor quality vesicles, many of which had broken up.

EXAMPLE 3

In this Example, more lipid vesicles in accordance with the present disclosure were made, employing a variety of glucoside primary amphiphiles.

TABLE 3

| | Sample | | | | | | | |
|---|---|---|---|---|---|---|---|---|
| | A | B | C | D | E | F | G | H |
| Glucoside primary amphiphile (g) | | | | | | | | |
| Myristyl glucoside[9] | 4.0 | 4.0 | | | | | | |
| Arachidyl behenyl glucoside[10] | | | 4.0 | 4.0 | | | | |
| Cocoyl glucoside[11] | | | | | 4.0 | 4.0 | | |
| Cetearyl glucoside[12] | | | | | | | 4.0 | 4.0 |
| Steroid (g) | | | | | | | | |
| Cholesterol | 1.0 | 1.0 | 1.0 | 1.0 | 1.0 | 1.0 | 1.0 | 1.0 |
| Encapsulated component(s) (g) | | | | | | | | |
| Propylene glycol dicaprate/caprate[13] | 30.0 | 40.0 | 30.0 | 40.0 | 30.0 | 40.0 | 30.0 | 40.0 |
| Other components (g) | | | | | | | | |
| Water | 50.0 | 50.0 | 50.0 | 50.0 | 50.0 | 50.0 | 50.0 | 50.0 |
| Processing temperature, °C. (lipid) | 75 | 75 | 75 | 75 | 75 | 75 | 75 | 75 |
| Processing temperature, °C. (aqueous) | 70 | 70 | 70 | 70 | 70 | 70 | 70 | 70 |

[9]MONTANOV 14
[10]MONTANOV 202
[11]MONTANOV 82
[12]MONTANOV 68, which includes a minor amount of cetearyl alcohol
[13]CAPTEX 200

Samples A and B produced "fluid white", small, spherical homogeneous paucilamellar vesicles (no free oil). Samples C and D produced larger, odder shaped but still acceptable paucilamellar vesicles. Samples E–H produced "solid white" very good small, spherical homogeneous paucilamellar vesicles. Sample F produced poor quality vesicles, many of which had broken up. Sample G produced very good small, spherical homogeneous paucilamellar vesicles. Sample H produced poor quality vesicles, many of which had broken up.

Equivalents

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. A paucilamellar lipid vesicle having 2–10 bilayers surrounding a large amorphous central cavity containing a water immiscible oily material, wherein each of said bilayers comprises a glucoside amphiphile and a steroid, wherein said glucoside amphiphile is selected from the group consisting of cocoyl glucoside, arachidyl behenyl glucoside, cetearyl glucoside and myristyl glucoside, and mixtures thereof.

2. The lipid vesicle of claim 1, wherein said steroid is a sterol selected from the group consisting of cholesterol, cholesterol derivatives, hydrocortisone, phytosterol, and mixtures thereof.

3. The lipid vesicle of claim 2 wherein said phytosterol is supplied from avocado oil unsaponifiables.

4. The lipid vesicle of claim 1 wherein said lipid bilayer(s) further comprise a minor amount of a secondary amphiphile which improves the shelf life stability of said lipid vesicles, said secondary amphiphile selected from the group consisting of $C_{12}$–$C_{18}$ fatty alcohols, polyoxyethylene acyl alcohols, polyglycerols, sorbitan fatty acid esters, ethoxylated sorbitan fatty acid esters, $C_{12}$–$C_{18}$ glycol monoesters, $C_{12}$–$C_{18}$ glyceryl mono- and diesters, propylene glycol stearate, sucrose distearate, glyceryl dilaurate, and mixtures thereof.

5. The lipid vesicle of claim 1, wherein said water immiscible oily material is selected from the group consisting of mineral oils, silicones, petrolatum, esters, paraffin waxes, triglyceride oils and fats, perfumes and fragrances, flavor oils, perfluorocarbon liquids, anthralin, water insoluble vitamins, water immiscible solvents, propylene glycol dicaprate, propylene glycol caprate, and mixtures thereof.

6. The lipid vesicle of claim 1 wherein said lipid bilayer(s) further comprise a charge producing agent selected from the group consisting of dimethyldistearyl amine, dicetyl phosphate, cetyl sulfate, phosphatidic acid, phosphatidyl serine, retinoic acid, oleic acid, palmitic acid, stearylamines and oleylamines, and mixtures thereof.

7. The lipid vesicle of claim 2, wherein said cholesterol derivative is ethyoxylated cholesterol.

8. The lipid vesicle of claim 5, wherein said triglyceride oil is a vegetable oil.

9. The lipid vesicle of claim 8, wherein said vegetable oil is soybean oil.

10. The lipid vesicle of claim 5, wherein said water insoluble vitamin is retinoic acid.

\* \* \* \* \*